United States Patent [19]

Morgan

[11] Patent Number: 4,533,657
[45] Date of Patent: Aug. 6, 1985

[54] ANALGESIC DIPEPTIDE AMIDES AND METHOD OF USE AND COMPOSITION THEREOF

[75] Inventor: Barry A. Morgan, Albany, N.Y.

[73] Assignee: Sterling Drug Inc., New York, N.Y.

[21] Appl. No.: 423,139

[22] Filed: Sep. 24, 1982

Related U.S. Application Data

[63] Continuation-in-part of Ser. No. 286,672, Jul. 24, 1981, abandoned.

[51] Int. Cl.$^3$ .................... A61K 37/00; C07C 103/52
[52] U.S. Cl. ...................................... 514/19; 514/809; 260/112.5 E
[58] Field of Search ................... 260/112.5 B, 112.5 R

[56] References Cited

U.S. PATENT DOCUMENTS

| | | | |
|---|---|---|---|
| 4,127,535 | 11/1978 | Coy et al. | 260/112.5 R |
| 4,178,371 | 12/1979 | Morgan | 260/112.5 E |
| 4,261,883 | 4/1981 | Smolarsky | 260/112.5 E |
| 4,350,627 | 9/1982 | de Costiglione et al. | 260/112.5 E |
| 4,380,535 | 4/1983 | Sarantakis | 260/112.5 E |

OTHER PUBLICATIONS

McGregor, et al., Life Sciences, 23, 1371–1378 (1978).
Roques, et al., European J. of Pharmacology, 60, (1979) 109–110.

*Primary Examiner*—Delbert R. Phillips
*Attorney, Agent, or Firm*—Theodore C. Miller; Paul E. Dupont; B. Woodrow Wyatt

[57] ABSTRACT

A genus of dipeptide amides including as the preferred subgenus the dipeptide amides having the structural formula HTyrD-AlaNR$_2$R$_3$ wherein R$_2$ is phenylalkyl or substituted-phenylalkyl and R$_3$ is hydrogen, alkyl, phenylalkyl, substituted-phenylalkyl or X-alkyl wherein X is an electronegative moiety are prepared by condensing the dipeptide with the amine or the amino acid with the amino acid amide and are useful as analgesics.

14 Claims, No Drawings

ANALGESIC DIPEPTIDE AMIDES AND METHOD OF USE AND COMPOSITION THEREOF

CROSS-REFERENCE TO RELATED APPLICATION

This application is a continuation-in-part of my co-pending application Ser. No. 286,672 filed July 24, 1981 and now abandoned.

BACKGROUND OF THE INVENTION

1. Field of the Invention

The invention relates to dipeptide amides which are useful as analgesics.

2. Description of the Prior Art

Coy and Kastin U.S. Pat. No. 4,127,535 describes

H-Tyr-X-Y wherein: X is a chiral residue of a D-amino acid selected from the group consisting of D-alanine, D-leucine, D-isoleucine, D-valine, D-phenylalanine, D-tyrosine, D-trytophan, D-serine, D-threonine, D-methionine, D-glutamic acid, D-glutamine, D-proline[,] D-aspartic acid, D-asparagine, D-lysine, D-arginine and D-histidine; and Y is selected from the group consisting of hydroxy, amino, loweralkylamino, diloweralkylamino and lower alkoxy which are stated to be useful as analgesic, tranqualizer, sedative, hypnotic, anti-depressant[,] prolactin releasing and growth hormone releasing agents and which are designated in the illustrative examples as derivatives of β-lipotropin fragment 61–62. Example 34 specifically describes D-Ala$^2$-β-lipotropin fragment 61–62 amide by name and method of preparation but does not describe any chemical or biological properties thereof.

McGregor (et al., Life Sciences, vol. 23, no. 13, pp. 1371–1378, 1978) describes H-Tyr-D-Ala-NH$_2$ (D-Ala$^2$-β-lipotropin fragment 61–62) amide and shows that it is greater than 10 times less potent intravenously and 200 times less potent intraventricularly in the tail flick test for analgesia in the rat, and binds to the opiate receptor in rat brain membranes with 830 times less affinity, than morphine.

Roques (et al., European Journal of Pharmacology, vol. 60, pp. 109–110, 1979) describes HTyrD-AlaNH(CH$_2$)$_2$NH(CH$_2$)$_2$Phenyl, which was less then 1% as potent as Met-enkephalin in both the guinea pig ileum and mouse vas deferens tests.

SUMMARY OF THE INVENTION

In a composition of matter aspect the invention is 2-(L-tyrosylamino)-2-R$_1$-N-R$_2$-N-R$_3$-acetamide having the structural formula Formula I HO—⟨phenyl⟩—CH$_2$—CH(NH$_2$)—CONH—C(R$_1$)(H)—CONR$_2$R$_3$ wherein R$_1$ is alkyl of one to five carbon atoms;

R$_2$ is CHQ(CH$_2$)$_n$Y wherein n is an integer from 1 through 9, Q is hydrogen or methyl, and Y is phenyl or phenyl substituted by fluoro, chloro, methyl, methoxy or trifluoromethyl; and R$_3$ is hydrogen, alkyl of one to five carbon atoms, or is selected from the group consisting of CHQ(CH$_2$)$_n$Y as defined for R$_2$ and (CH$_2$)$_m$X wherein m is an integer from 1 through 4 and X is amino, methylamino, dimethylamino, dimethyloxoamino, acetamido, N-methylacetamido, methylthio, methylsulfinyl, methylsulfonyl, hydroxy, carboxy, carbamoyl, methylcarbamoyl or dimethylcarbamoyl;

or a pharmaceutically acceptable acid addition salt thereof.

The compounds of Formula I are useful as analgesics.

In a first process aspect the invention is the process of preparing 2-(L-tyrosylamino)-2-R$_1$-N-R$_2$-N-R$_3$-acetamide of Formula I which comprises condensing L-tyrosine with the corresponding 2-NH$_2$-2-R$_1$-acetic acid to form the corresponding 2-(L-tyrosylamino)-2-R$_1$-acetic acid and then condensing said 2-(L-tyrosylamino)-2-R$_1$-acetic acid with the corresponding HNR$_2$R$_3$, concomitantly protecting and deprotecting the α-amino, tyrosyl phenolic hydroxyl and acetyl carboxyl groups as required.

In a second process aspect the invention is the process of preparing 2-(L-tyrosylamino)-2-R$_1$-N-R$_2$-N-R$_3$-acetamide of Formula I which comprises condensing L-tyrosine with the corresponding 2-NH$_2$-2-R$_1$-acetic acid methyl ester to form the corresponding 2-(L-tyrosylamino)-2-R$_1$-acetic acid methyl ester, then condensing said 2-(L-tyrosylamino)-2-R$_1$-acetic acid methyl ester with hydrazine to form 2-(L-tyrosylamino)-2-R$_1$-acetyl hydrazide, then reacting said 2-(L-tyrosylamino)-2-R$_1$-acetyl hydrazide with an alkyl nitrite to form 2-(L-tyrosylamino)-2-R$_1$-acetyl azide, then condensing said 2-(L-tyrosylamino)-2-R$_1$-acetyl azide with the corresponding HNR$_2$R$_3$, concomitantly protecting and deprotecting the α-amino and tyrosyl phenolic hydroxyl groups as required.

In a third process aspect the invention is the process of preparing 2-(L-tyrosylamino)-2-R$_1$-N-R$_2$-N-R$_3$-acetamide of Formula I which comprises condensing the corresponding 2-NH$_2$-2-R$_1$-acetic acid with the corresponding HNR$_2$R$_3$ to form the corresponding 2-NH$_2$-2-R$_1$-N-R$_2$-N-R$_3$-acetamide and then condensing said 2-NH$_2$-2-R$_1$-N-R$_2$-N-R$_3$-acetamide with L-tyrosine, concomitantly protecting and deprotecting the α-amino and tyrosyl phenolic hydroxyl groups as required.

In a method of use aspect the invention is the method of producing analgesia in a mammal in pain which comprises administering to the mammal an analgesically effective amount of 2-(L-tyrosylamino)-2-R$_1$-N-R$_2$-N-R$_3$-acetamide of Formula I or a pharmaceutically acceptable acid addition salt thereof.

In another composition of matter aspect the invention is a pharmaceutical composition for producing analgesia in a mammal consisting essentially of an analgesically effective concentration of 2-(L-tyrosylamino)-2-R$_1$-N-R$_2$-N-R$_3$-acetamide of Formula I or a pharmaceutically acceptable acid addition salt thereof and a pharmaceutically acceptable vehicle.

When R$_1$ or R$_3$ of Formula I is alkyl of one to five carbon atoms, it can be any of the possible primary, secondary and tertiary alkyls of one to five carbon atoms, especially including methyl, ethyl, n-propyl, isopropyl, n-butyl, tert-butyl, n-pentyl and 3-methylbutyl.

In a preferred composition of matter aspect the invention is L-tyrosyl-N-R$_2$-N-R$_3$-D-alaninamide having the structural formula HTyrD-AlaNR$_2$R$_3$  Formula II, which is the compound of Formula I wherein R$_1$ is methyl, or a pharmaceutically acceptable acid addition salt thereof.

In a most preferred composition of matter aspect the invention is the following compounds of Formula II, which are the free base forms of the compounds of the examples whose preparation and biological properties are described below.

| Compound of Formula II | Example |
|---|---|
| HTyrD-AlaNH(CH$_2$)$_2$Ph | 1 |
| HTyrD-AlaN(CH$_2$)$_3$Ph / Me | 2 |
| HTyrD-AlaNH(CH$_2$)$_3$Ph | 3 |
| HTyrD-AlaN(CH$_2$)$_3$Ph / Et | 4 |
| HTyrD-AlaNH(CH$_2$)$_4$Ph | 5 |
| HTyrD-AlaNH(CH$_2$)$_5$Ph | 6 |
| HTyrD-AlaN(CH$_2$)$_3$Ph / (CH$_2$)$_2$NMe$_2$ | 7 |
| HTyrD-AlaNHC(Me)(H)(CH$_2$)$_2$Ph | 8 |
| HTyrD-AlaNHC(H)(Me)(CH$_2$)$_2$Ph | 9 |
| HTyrD-AlaN(CH$_2$)$_3$Ph / (CH$_2$)$_3$SMe | 10 |
| HTyrD-AlaN(CH$_2$)$_3$Ph / (CH$_2$)$_3$SOMe | 11 |

In Formula II and the foregoing formulas of specific compounds of Formula II
Tyr represents L-tyrosyl,
D-Ala represents D-alanyl,
Ph represents phenyl,
Me represents methyl, and
Et represents ethyl.
The symbols Tyr and D-Ala do not include the N-terminal and C-terminal groups. R$_2$ and R$_3$ of Formula II are the same as R$_2$ and R$_3$ of Formula I.

DETAILED DESCRIPTION OF THE INVENTION INCLUSIVE OF THE PREFERRED EMBODIMENTS

PREPARATION OF THE COMPOUNDS

The protection, activation, condensation and deprotection steps required to prepare the compounds of Formula I are carried out using the methods of peptide synthesis generally described by Houben Weyl "Methoden der Organischen Chemie" (vol. 16, parts I and II, "Synthese von Peptiden", Thieme, 1974) and Gross and Meienhofer "The Peptides" (vol. 1, "Major Methods of Peptide Bond Formation", Academic Press, 1979).

The suitably carboxyl-activated derivatives of the amino acid and dipeptide intermediates can be formed and used with or without being isolated and include the acyl halides and pseudohalides, especially the acyl azides; the anhydrides, especially the mixed anhydrides and most especially the mixed anhydride with diphenylphosphinyl chloride, isobutyl chloroformate or pivalyl chloride; derivatives formed by addition reactions, especially using dicyclohexylcarbodiimide; displaceable acyl derivatives of heterocyclic nitrogen; ring-openable activated heterocyclic systems; acylphosphonium derivatives; activated esters, especially N-hydroxysuccinimide, nitrophenyl and pentafluorophenyl esters; and polymeric (solid phase) derivatives.

It is necessary that the N-terminal α-amino function be protected during the amide forming steps. It is preferred but not essential that the tyrosyl phenolic hydroxyl also be protected. The preferred α-amino protecting groups are benzyloxycarbonyl (Z), which can be removed by catalytic hydrogenation using palladium as catalyst or by hydrogen bromide in acetic acid, and tert-butyloxycarbonyl (Boc), which can be removed by acidic cleavage, for example, with hydrogen chloride in a suitable solvent or trifluoroacetic acid. Benzyl (Bz) and tert-butyl (tBu) are the preferred tyrosyl phenolic hydroxyl protecting groups. Benzyl can be removed by catalytic hydrogenation using palladium as catalyst or by hydrogen bromide in acetic acid. tert-Butyl can be removed by acidic cleavage, for example, with hydrogen chloride in a suitable solvent or trifluoroacetic acid.

The C-terminal carboxyl group must be protected during the peptide forming step. In the first process aspect it is protected as the amide, which is, of course, not removed. In the second process aspect the methyl ester protects the carboxyl group during peptide bond formation and subsequently activates it for hydrazide bond formation. In the third process aspect the C-terminal carboxyl group can be protected as the carboxylate salt, the t-butyl ester, which can be removed by acidic cleavage, for example, with hydrogen chloride in a suitable solvent or trifluoroacetic acid, or the benzyl ester, which can be removed by catalytic hydrogenation using palladium as catalyst.

The unprotected and protected L-tyrosine, unprotected and protected 2-NH$_2$-2-R$_1$-acetic acid, 2-NH$_2$-2-R$_1$-acetic acid methyl ester and HNR$_2$R$_3$ starting materials are known classes of compounds. The individual compounds are commercially available or can be made by methods specifically or generally described in the chemical literature.

Besides being preparable by the three process aspects of the invention the compounds of Formulas I and II wherein R$_3$ is (CH$_2$)$_m$X and X is dimethyloxoamino, methylsulfinyl and methylsulfonyl can also be prepared by oxidation by known methods of the respective corresponding compounds of Formulas I and II wherein $R_3$ is $(CH_2)_mX$ and X is dimethylamino and methylthio.

The acid addition salts of the compounds of Formula I are prepared by conventional methods from any of the pharmaceutically acceptable organic and inorganic acids. Of the inorganic acids hydrochloric acid and phosphoric acid are particularly preferred. Of the organic acids acetic acid is particularly preferred.

The compounds of Formula I and the acid addition salts thereof are hydrophilic and may form solvates with water or hydrophilic organic solvents or mixtures thereof. If the resulting products are crystalline, they are purified by recrystallization. If they are non-crystalline, which is generally so, they are purified by high pressure liquid chromatography or column chromatography and/or isolated by lyophilization.

In the preparations described below structures of products are inferred from known structures of starting materials and expected courses of preparative reactions. Structural confirmation and estimation of purity of starting materials and products are measured by melting temperature range (m.r.), optical rotation ($[\alpha]_D^{25}$), elemental analysis, infrared (IR) spectral analysis, ultraviolet (UV) spectral analysis, mass spectral (MS) analysis, nuclear magnetic resonance (NMR) spectral analysis, gas chromatography (GLC), high pressure liquid chromatography (HPLC), thin layer chromatography (TLC) and/or amino acid analysis.

EXAMPLE 1

HTyrD-AlaNH(CH$_2$)$_2$Ph

A. ZTyr(Bz)D-AlaOMe

Triethylamine (5.7 ml.), then isobutylchloroformate (5.3 ml.), were added with stirring to a solution of N-benzyloxycarbonyl-O-benzyl-L-tyrosine (16.68 g.) in acetone (175 ml.) maintained at −20° C. The solution was stirred for 10 minutes at −20° C., then D-alanine methyl ester hydrochloride (6.4 g.) and triethylamine (5.7 ml.) in chloroform (65 ml.) were added. Stirring was continued one hour at this temperature, then four hours at room temperature. The mixture was filtered and the filtrate was stripped of volatiles. The residue and the filtration solid were combined and distributed between water (200 ml.) and ethyl acetate (250 ml.). Part of the product was collected by filtration and washed with aqueous hydrochloric acid, water, saturated sodium bicarbonate and water. The ethyl acetate layer was washed with cold aqueous hydrochloric acid (0.5N), water, saturated aqueous sodium bicarbonate, water again and saturated aqueous sodium chloride and stripped of volatiles, yielding another part of the product. The two parts were combined and recrystallized from absolute ethanol, affording (N-benzyloxycarbonyl-O-benzyl-L-tyrosyl)-D-alanine methyl ester (15.28 g.; m.r. 161°–163° C.; $[\alpha]_D^{25}$ −11.7°, c=2, dimethylformamide)

B. ZTyr(Bz)D-AlaNHNH$_2$

A solution of hydrazine hydrate (5.05 ml.) in ethanol (45 ml.) was added to a solution of (N-benzyloxycarbonyl-O-benzyl-L-tyrosyl)-D-alanine methyl ester (15.18 g.) in tetrahydrofuran (135 ml.). The resulting solution was stirred at room temperature and seeded. (N-Benzyloxycarbonyl-O-benzyl-L-tyrosyl)-D-alanyl hydrazide (13.2 g.; m.r. 216°–218° C.; $[\alpha]_D^{25}$ −21.4°, c=2, dimethylformamide) separated from the solution as a crystalline solid.

C. ZTyr(Bz)D-AlaNH(CH$_2$)$_2$Ph n-Butyl nitrite (0.65 ml.) was added with stirring to a solution of (N-benzyloxycarbonyl-O-benzyl-L-tyrosyl)-D-alanyl hydrazide (2.5 g.), hydrogen chloride in dimethylformamide (3.3N, 1.4 ml.) and dimethylformamide (10 ml.) maintained at ice-water temperature. 2-Phenylethylamine (0.61 g.) was added, stirring was continued for 15 minutes, and the mixture was refrigerated at about 5° C. overnight, then poured into water (300 ml.). Recrystallization of the resulting solid from methanol afforded (N-benzyloxycarbonyl-O-benzyl-L-tyrosyl)-N-(2-phenylethyl)-D-alaninamide in two crops (1.75 g., m.r. 169°–171° C.; 0.41 g., m.r. 165°–167° C.).

D. HTyrD-AlaNH(CH$_2$)$_2$Ph

A mixture of (N-benzyloxycarbonyl-O-benzyl-L-tyrosyl)-N-(2-phenylethyl)-D-alaninamide (1.5 g.), palladium on carbon (10%, 0.3 g.) and acetic acid (total volume, 50 ml.) was hydrogenated at room temperature under pressure (40–50 p.s.i.g., uptake 91% at 50 minutes). The mixture was filtered and the filtrate was concentrated under vacuum (0.05 mm. of mercury). Water was added to the residual glass, the solution was again concentrated, and the procedure was repeated with filtration. Nuclear magnetic resonance spectral analysis of the product (530 mg.) showed that it had the expected structure and was an acetate salt. Part (416 mg.) was dissolved in aqueous hydrochloric acid (0.0936, 20 ml.), and the solution was lyophilized. An aqueous solution of the residue was filtered and lyophilized, affording as an amorphous white solid L-tyrosyl-N-(2-phenylethyl)-D-alaninamide monohydrochloride hydrate (4:5) (388 mg.; $[\alpha]_D^{25}$ +61.1°, c=1, methanol), whose free base is the compound of Formula II wherein $R_2$ is CHQ(CH$_2$)$_n$Y wherein n is 1, Y is phenyl and Q is hydrogen and $R_3$ is hydrogen.

EXAMPLE 2

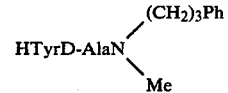

By the method of Example 1, using 1.47 g. of (N-benzyloxycarbonyl-O-benzyl-L-tyrosyl)-D-alanyl hydrazide and substituting N-methyl-3-phenylpropylamine hydrochloride (0.56 g.) for 2-phenylethylamine in part C thereof, and lyophilizing the final product, there was obtained as an amorphous white solid L-tyrosyl-N-methyl-N-(3-phenylpropyl)-D-alaninamide monohydrochloride monohydrate (311 mg.), whose free base is the compound of Formula II wherein $R_2$ is CHQ(CH$_2$)$_n$Y wherein n is 2, Y is phenyl and Q is hydrogen and $R_3$ is methyl.

EXAMPLE 3

HTyrD-AlaNH(CH$_2$)$_3$Ph

By the method of Example 1, using 4.9 g. of (N-benzyloxycarbonyl-O-benzyl-L-tyrosyl)-D-alanyl hydrazide and substituting 3-phenylpropylamine (1.45 ml.) for 2-phenylethylamine in part C thereof, and lyophilizing the final product, there was obtained as an amorphous white solid L-tyrosyl-N-(3-phenylpropyl)-D-alaninamide monohydrochloride sesquihydrate (453 mg.), whose free base is the compound of Formula II wherein $R_2$ is CHQ(CH$_2$)$_n$Y wherein n is 2, Y is phenyl and Q is hydrogen and $R_3$ is hydrogen.

EXAMPLE 4

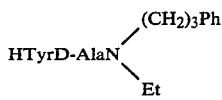

By the method of Example 1, using 2.45 g. of (N-benzyloxycarbonyl-O-benzyl-L-tyrosyl)-D-alanyl hydrazide and substituting N-ethyl-3-phenylpropylamine hydrochloride (2.0 g.) for 2-phenylethylamine in part C thereof, and lyophilizing the final product, there was obtained as an amorphous white solid L-tyrosyl-N-ethyl-N-(3-phenylpropyl)-D-alaninamide monohydrochloride (530 mg.; $[\alpha]_D^{25} + 59.9°$, c=1, methanol), whose free base is the compound of Formula II wherein $R_2$ is $CHQ(CH_2)_nY$ wherein n is 2, Y is phenyl and Q is hydrogen and $R_3$ is ethyl.

EXAMPLE 5

HTyrD-AlaNH(CH$_2$)$_4$Ph

By the method of Example 1, using 1.47 g. of (N-benzyloxycarbonyl-O-benzyl-L-tyrosyl)-D-alanyl hydrazide and substituting 4-phenylbutylamine (0.45 g.) for 2-phenylethylamine in part C thereof, and lyophilizing the final product, there was obtained as an amorphous pale yellow solid L-tyrosyl-N-(4-phenylbutyl)-D-alaninamide monohydrochloride (474 mg.; $[\alpha]_D^{25} + 60.5°$, c-1, methanol), whose free base is the compound of Formula II wherein $R_2$ is $CHQ(CH_2)_nY$ wherein n is 3, Y is phenyl and Q is hydrogen and $R_3$ is hydrogen.

EXAMPLE 6

HTyrD-AlaNH(CH$_2$)$_5$Ph

By the method of Example 1, using 1.67 g. of (N-benzyloxycarbonyl-O-benzyl-L-tyrosyl)-D-alanyl hydrazide and substituting 5-phenylpentylamine (550 mg.) for 2-phenylethylamine in part C thereof, and lyophilizing the final product, there was obtained as an amorphous off-white solid L-tyrosyl-N-(5-phenylpentyl)-D-alaninamide monohydrochloride monohydrate (59 mg.), whose free base is the compound of Formula II wherein $R_2$ is $CHQ(CH_2)_nY$ wherein n is 4, Y is phenyl and Q is hydrogen and $R_3$ is hydrogen.

EXAMPLE 7

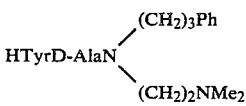

By the method of Example 1, using 2.94 g. of (N-benzyloxycarbonyl-O-benzyl-L-tyrosyl)-D-alanyl hydrazide and substituting N-[2-(dimethylamino)ethyl]-3-phenylpropylamine (prepared by reductive condensation of 3-phenylpropionaldehyde and N,N-dimethyl-1,2-ethanediamine with sodium cyanoborohydride; also prepared by acylation of N,N-dimethyl-1,2-ethanediamine with 3-phenylpropionyl chloride followed by reduction of the resulting amide with lithium aluminum hydide; b.r. 107°–110° C./0.3 mm.; 1.24 g.) for 2-phenylethylamine in part C thereof, and lyophilizing the final product, there was obtained as an amorphous light yellow solid L-tyrosyl-N-[2-(dimethylamino)ethyl]-N-(3-phenylpropyl)-D-alaninamide dihydrochloride (194 mg.), whose free base is the compound of Formula II wherein $R_2$ is $CHQ(CH_2)_nY$ wherein n is 2, Y is phenyl and Q is hydrogen and $R_3$ is $(CH_2)_mX$ wherein m is 2 and X is dimethylamino.

EXAMPLE 8

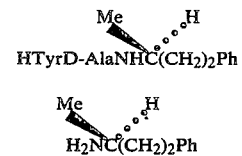

(S)-1-Methyl-3-phenylpropanamine hydrochloride was prepared by first esterifying N-(tert-butyloxycarbonyl)-L-alanine with diazomethane, then reducing the resulting N-(tert-butyloxycarbonyl)-L-alanine methyl ester with diisobutylaluminum hydride, then condensing the resulting N-(tert-butyloxycarbonyl)-L-alaninal with benzylidenetriphenylphosphonium ylide, then hydrogenating over palladium catalyst the resulting [S-(E)]-N-(tert-butyloxycarbonyl)-1-methyl-3-phenyl-2-propenamine having m.r. 86°–88° C. and $[\alpha]_D^{25}$ (c=1, methanol) −50.9°, and finally deprotecting with hydrogen chloride in dioxane the resulting (S)-N-(tert-butyloxycarbonyl)-1-methyl-3-phenylpropanamine having m.r. 78°–80° C. and $[\alpha]_D^{25} - 7.1°$ (c=1, methanol).

To a solution of N-(tert-butyloxycarbonyl)-O-(tert-butyl)-L-tyrosyl-D-alanine (816 mg.) in tetrahydrofuran (25 ml.) maintained at −20° C. were added with stirring first a solution of N-methylmorpholine (202 mg.) in tetrahydrofuran (5 ml.), then a solution of isobutyl chloroformate (274 mg.) in tetrahydrofuran (5 ml.), and finally a solution of (S)-1-methyl-3-phenylpropanamine hydrochloride (372 mg.) and N-methylmorpholine (202 mg.) in tetrahydrofuran (25 ml.). The resulting mixture was stirred and maintained at −20° C. for one hour, then diluted with ethyl acetate (200 ml.). The resulting mixture was washed with water (100 ml.), aqueous citric acid (5%, 2×70 ml.), saturated aqueous sodium bicarbonate (2×70 ml.) and saturated aqueous sodium chloride, dried over magnesium sulfate, filtered and stripped of volatiles under vacuum. High pressure liquid chromatography of the resulting solid (1.10 g.) on silica gel (350 g.) using hexane-ethyl acetate (2:3) as the eluant (100 ml./min.) afforded in fractions with k′=2.5–4.5 N-(tert-butyloxycarbonyl)-O-(tert-butyl)-L-tyrosyl-N-(1-S-methyl-3-phenylpropyl)-D-alaninamide as a white foam (954 mg.; $[\alpha]_D^{25} + 34.4°$, c=1, methanol.

A solution of N-(tert-butyloxycarbonyl)-O-(tert-butyl)-L-tyrosyl-N-(1-S-methyl-3-phenylpropyl)-D-alaninamide (850 mg.) in hydrogen chloride-dioxane (3.9N, 25 ml.) was stirred for one hour at room temperature, then stripped of volatiles under vacuum. Lyophilization of a solution of the residue in water (40 ml.)

afforded as an amorphous white solid L-tyrosyl-N-(1-S-methyl-3-phenylpropyl)-D-alaninamide. monohydrochloride (664 mg.; $[\alpha]_D^{25}+49.5°$, c=1, methanol), whose free base is the compound of Formula II wherein $R_2$ is $CHQ(CH_2)_nY$ wherein n is 2, Y is phenyl, Q is methyl and the chirality of the carbon atom bearing Q is S and $R_3$ is hydrogen.

EXAMPLE 9

HTyrD-AlaNHC(CH₃)(H)(CH₂)₂Ph

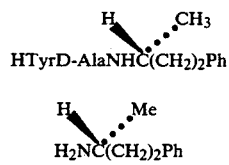   A.

(R)-1-Methyl-3-phenylpropanamine hydrochloride was prepared by first esterifying N-(tert-butyloxycarbonyl)-D-alanine with diazomethane, then reducing the resulting N-(tert-butyloxycarbonyl)-D-alanine methyl ester with diisobutylaluminum hydride, then condensing the resulting N-(tert-butyloxycarbonyl)-D-alaninal with benzylidenetriphenylphosphonium ylide, then hydrogenating over palladium catalyst the resulting [R-(E)]-N-(tert-butyloxycarbonyl)-1-methyl-3-phenyl-2-propenamine having m.r. 86°–88° C. and $[\alpha]_D^{25}+54.0°$ (c=1, methanol), and finally deprotecting with hydrogen chloride in dioxane the resulting (R)-N-(tert-butyloxycarbonyl)-1-methyl-3-phenylpropanamine having m.r. 74°–76° C. and $[\alpha]_D^{25}+7.2°$ (c=1, methanol).

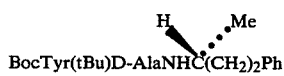   B.

BocTyr(tBu)D-AlaNHC(CH₃)(H)(CH₂)₂Ph

By the method of part B of Example 8, N-(tert-butyloxycarbonyl)-O-(tert-butyl)-L-tyrosyl-D-alanine (816 mg.) was condensed with (R)-1-methyl-3-phenylpropanamine hydrochloride (375 mg.) and the product was purified by high pressure liquid chromatography, affording N-(tert-butyloxycarbonyl)-O-(tert-butyl)-L-tyrosyl-N-(1-R-methyl-3-phenylpropyl)-D-alaninamide as a white foam (982 mg.; $[\alpha]_D^{25}+38.2°$, c=1, methanol).

   C.

HTyrD-AlaNHC(CH₃)(H)(CH₂)₂Ph

A solution of N-(tert-butyloxycarbonyl)-O-(tert-butyl)-L-tyrosyl-N-(1-R-methyl-3-phenylpropyl)-D-alananinamide (890 mg.) in hydrogen chloride-dioxane (3.9N, 25 ml.) was stirred for one and one half hours at room temperature, then stripped of volatiles under vacuum. Lyophilization of a solution of the residue in water (40 ml.) afforded as an amorphous white solid L-tyrosyl-N-(1-R-methyl-3-phenylpropyl)-D-alaninamide monohydrochloride (661 mg.; $[\alpha]_D^{25}+71.1°$, c=1, methanol), whose free base is the compound of Formula II wherein $R_2$ is $CHQ(CH_2)_nY$ wherein n is 2, Y is phenyl, Q is methyl and the chirality of the carbon atom bearing Q is R and $R_3$ is hydrogen.

EXAMPLE 10

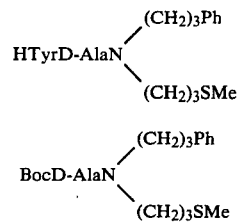

A solution of N-(tert-butyloxycarbonyl)-D-alanine pentafluorophenyl ester (3.55 g.) and N-[3-(methylthio)propyl]-3-phenylpropanamine (prepared by acylation of 3-(methylthio)propylamine with 3-phenylpropionyl chloride followed by reduction of the resulting amide with lithium aluminum hydride; b.r. 108°–112° C./0.05 mm.; 2.23 g.) in tetrahydrofuran (10 ml.) was stirred for one hour at 0° C., then 68 hours at room temperature, then stripped of volatiles under vacuum. A solution of the residue in ethyl acetate was washed once with aqueous citric acid (5%), twice with saturated aqueous sodium bicarbonate and once with saturated aqueous sodium chloride, dried over magnesium sulfate, and stripped of ethyl acetate. High pressure liquid chromatography of the resulting oil (5.5 g.) on silica gel (350 g.) using hexane-ethyl acetate (4:1) as the eluant (50–100 ml./min.) afforded in fractions with k'=4–8 $N^2$-(tert-butyloxycarbonyl)-N-[3-(methylthio)propyl]-N-(3-phenylpropyl)-D-alaninamide as a pale yellow oil (3.3 g.; $[\alpha]_D^{25}+17.7°$, c=1, methanol), whose NMR spectrum showed one-half mole of ethyl acetate per mole of product.

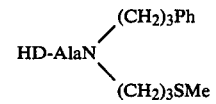   B.

A solution of $N^2$-(tert-butyloxycarbonyl)-N-[3-(methylthio)propyl]-N-(3-phenylpropyl)-D-alaninamide hemiethyl acetate (1.975 g.) in hydrogen chloride-dioxane (3.9N, 25 ml.) was stirred for two hours at room temerpature, then stripped of volatiles under vacuum, affording N-[3-(methylthio)propyl]-N-(3-phenylpropyl)-D-alaninamide hydrochloride as a viscous oil (1.474 g.).

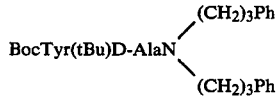   C.

By the method of part B of Example 8, N-(tert-butyloxycarbonyl)-O-(tert-butyl)-L-tyrosine (1.50 g.) was condensed with N-[3-(methylthio)propyl]-N-(3-phenylpropyl)-D-alaninamide hydrochloride (1.470 g.), affording N-(tert-butyloxycarbonyl)-O-(tert-butyl)-L-tyrosyl-N-[3-(methylthio)propyl]-N-(3-phenylpropyl)-D-alaninamide as a viscous oil (2.716 g.).

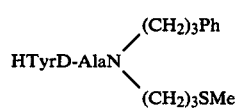   D.

A solution of N-(tert-butyloxycarbonyl)-O-(tert-butyl)-L-tyrosyl-N-[3-(methylthio)propyl]-N-(3-phenylpropyl)-D-alaninamide (2.42 g.) in hydrogen chloride-dioxane (3.9N, 50 ml.) was stirred for one and one half hours at room temperature, then stripped of volatiles under vacuum. The residue was triturated with ether, the solution was stripped of volatiles under vacuum, and the process was repeated. An aqueous solution of the residue was lyophilized. A solution of the residue in methanol (50 ml.) was stripped of volatiles, affording a white foam (1.960 g.). Part (950 mg.) of the white foam was twice more lyophilized, affording as an amorphous white solid L-tyrosyl-N-[3-(methylthio)propyl]-N-(3-phenylpropyl)-D-alaninamide monhydrochloride hemihydrate (675 mg.; $[\alpha]_D^{25}+57.0$, c=1, methanol), whose free base is the compound of Formula II wherein $R_2$ is $CHQ(CH_2)_nY$ wherein n is 2, Y is phenyl and Q is hydrogen and $R_3$ is $(CH_2)_mX$ wherein m is 3 and X is methylthio.

EXAMPLE 11

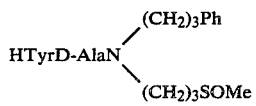

A solution of L-tyrosyl-N-[3-(methylthio)propyl]-N-(3-phenylpropyl)-D-alaninamide monohydrochloride (987 mg.) and aqueous hydrogen peroxide (3%, 2.50 ml.) in glacial acetic acid (20 ml.) was stirred for two hours at room temperature, then stripped of volatiles under vacuum. Stripping was repeated five times after twice adding ethyl acetate and thrice adding ether to the residue. The product was lyophilized, affording as an amorphous white solid L-tyrosyl-N-[3-(methylsulfinyl)propyl]-N-(3-phenylpropyl)-D-alaninamide monohydrochloride (999 mg.; $[\alpha]_D^{25}+49.1°$, c=1, methanol), whose free base is the compound of Formula II wherein $R_2$ is $CHQ(CH_2)_nY$ wherein n is 2, Y is phenyl and Q is hydrogen and $R_3$ is $(CH_2)_mX$ wherein m is 3 and X is methylsulfinyl.

BIOLOGICAL PROPERTIES OF THE COMPOUNDS

As stated above the compounds of Formula I are useful as analgesic agents. This utility has been shown by the results of testing the examples in vitro in the guinea pig ileum test. Some of the examples have also been shown to be active in vivo in the mouse acetylcholine writhing test.

Guinea Pig Ileum Test

Adult male guinea pigs (Charles River, Hartley strain) weighing 300–500 g. are decapitated, and the terminal ileum is exposed by reflecting the overlying cecum, severed at the ileocecal juncture, and removed while cutting the mesenteric attachments to avoid excessive traction on the tissue. The ileum (about 30 cm. in length) is transferred to a beaker containing warm modified Krebs-Henseleit solution (118 mM sodium chloride, 4.75 mM potassium chloride, 2.45 mM calcium chloride, 1.19 mM potassium dihydrogen phosphate, 1.2 mM magnesium sulfate, 25 mM sodium bicarbonate, 11 mM glucose, 20 µM choline chloride and 0.125 µM pyrilamine maleate). The terminal (aboral) portion (about 10 cm. in length) is discarded, and segments (3–4 cm. in length) are cut from the remainder and gently slid onto a glass rod (5–6 mm. in diameter) and arranged so that the mesenteric attachment is in a straight line. A cotton swab moistened in the solution is then carefully used to separate the longitudinal muscle from the underlying circular muscle. The longitudinal muscle and adhering myenteric plexus is then gently removed from the remaining tissue with forceps.

Strips of thus prepared longitudinal muscle are mounted in a double-jacketed organ bath (5 ml.) under tension (1.0 g.), connected to isometric transducers (Grass FT 0.03), bathed in the modified Krebs-Henseleit solution described above, aerated with oxygen-carbon dioxide (95:5) and maintained at 37° C.

Stimulators (Grass S-44) are set to deliver repetitive monphasic square wave field stimulation (supramaximal voltage, 0.10 Hz., 0.25 msec. duration) through platinum ring electrodes at the top and bottom of the bath. Regular contractions of the muscle, which result from electrically-induced liberation of acetylcholine from postganglionic parasympathetic nerves, are recorded on a polygraph (Grass model 5). Following tissue equilibration (45–60 min.) and repeated washing (every 10 min.) an aqueous solution of a reference or test compound is added to the bath in a microliter volume (1.25–250 µl) and reductions in muscle twitch height are recorded. More compound can be added with (single dose method) or without (cumulative dose method) first washing the preparation.

From the results a half-maximal inhibitory concentration (IC50) value for the compound is computed by regression analysis of a linear plot of logarithm of concentration against percent of inhibition of twitch height (probits). The ratio of the IC=value of a reference compound to that of a test compound tested in the same preparation is the molar potency ratio. Usually four preparations are tested simultaneously by the same person (N=4), and the resulting four molar potency ratios are averaged.

The following results were obtained using the examples as test compounds and Met[5]-enkephalin as the reference compound:

| Compound | Average Molar Potency Ratio |
| --- | --- |
| Met[5]-enkephalin | 100 |
| Example 1 | 14 |
| Example 2 | 9 |
| Example 3 | 117 |
| Example 4 | 4 |
| Example 5 | 12 |
| Example 6 | 30 |
| Example 7 | 4 |
| Example 8 | 115 |
| Example 9 | 12 |
| Example 10 | 15 |
| Example 11 | 3 |

Mouse Acetylcholine Writhing Test

Male Swiss-Webster mice each weighing 18–24 g. are treated subcutaneously (10 ml./kg. injection volume) or orally with the test compound in an aqueous vehicle. Twenty minutes thereafter each mouse is injected intraperitoneally with acetylcholine (3.2 mg./kg.) in aqueous sodium chloride (0.9%). This dose of acetylcholine causes one or more characteristic writhes in the two minute period following injection in control mice which receive the aqueous vehicle not containing the test compound. A mouse not exhibiting the writhe during the two minute period is scored inhibited by the test compound. Test compounds are screened at doses of 100 and 30 mg./kg. subcutaneously and 300 and 100 mg./kg. orally using 15 mice at each dose level. ED50 values for active compounds are estimated by probit analysis of quantal scores at four or more dose levels using 15 mice at each dose level.

Approximate ED50 values were determined subcutaneously for some of the examples and are shown in the following table.

| Compound | ED50 (mg./kg.) |
| --- | --- |
| Example 2 | >10 |
| Example 3 | <30 >10 |
| Example 4 | >30 |

To carry out the method of use and pharmaceutical composition aspects of the invention the compounds of Formula I can be administered orally or parenterally in liquid or solid dosage form as solutions, suspensions, emulsions, capsules or tablets, which are prepared with conventional pharmaceutical vehicles and adjuncts by conventional pharmaceutical techniques.

I claim:

1. 2-(L-tyrosylamino)-2-$R_1$-N-$R_2$-N-$R_3$-acetamide having the structural formula

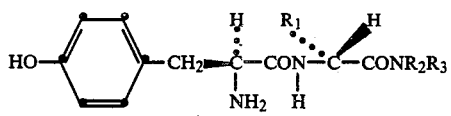

wherein $R_1$ is alkyl of one to five carbon atoms;

$R_2$ is $CHQ(CH_2)_nY$ wherein n is an integer from 1 through 9, Q is hydrogen or methyl, and Y is phenyl or phenyl substituted by fluoro, chloro, methyl, methoxy or trifluoromethyl; and $R_3$ is selected from the group consisting of $CHQ(CH_2)_nY$ as defined for $R_2$ and $(CH_2)_mX$ wherein m is an integer from 1 through 4 and X is amino, methylamino, dimethylamino, dimethyloxoamino, acetamido, N-methylacetamido, methylthio, methylsulfinyl, methylsulfonyl, hydroxy, carboxy, carbamoyl, methylcarbamoyl or dimethylcarbamoyl;

or a pharmaceutically acceptable acid addition salt thereof.

2. A compound according to claim 1 wherein $R_1$ is methyl and having the structural formula

or a pharmaceutically acceptable acid addition salt thereof.

3. A compound according to claim 2 wherein $R_3$ is $(CH_2)_mX$ or a pharmaceutically acceptable acid addition salt thereof.

4. A compound according to claim 3 wherein $R_2$ is $CHQ(CH_2)_nY$ wherein n is 3, Q is hydrogen and Y is phenyl or a pharmaceutically acceptable acid addition salt thereof.

5. A compound according to claim 4 wherein m is 2 or a pharmaceutically acceptable acid addition salt thereof.

6. The compound according to claim 5 wherein X is dimethylamino or a pharmaceutically acceptable acid addition salt thereof.

7. L-Tyrosyl-N-[2-(dimethylamino)ethyl]-N-(3-phenylpropyl)-D-alaninamide dihydrochloride according to claim 3.

8. A compound according to claim 4 wherein m is 3 or a pharmaceutically acceptable acid addition salt thereof.

9. The compound according to claim 8 wherein X is methylthio or a pharmaceutically acceptable acid addition salt thereof.

10. L-Tyrosyl-N-[3-(methylthio)propyl]-N-(3-phenylpropyl)-D-alaninamide monohydrochloride hemihydrate according to claim 9.

11. The compound according to claim 8 wherein X is methylsulfinyl or a pharmaceutically acceptable acid addition salt thereof.

12. L-Tyrosyl-N-[3-(methylsulfinyl)propyl]-N-(3-phenylpropyl)-D-alaninamide monohydrochloride according to claim 11.

13. The method of producing analgesia in a mammal in pain which comprises administering to the mammal an analgesically effective amount of 2-(L-tyrosylamino)-2-$R_1$-N-$R_2$-N-$R_3$-acetamide according to claim 1 or a pharmaceutically acceptable acid addition salt thereof.

14. A pharmaceutical composition for producing analgesia in a mammal consisting essentially of an analgesically effective concentration of 2-(L-tyrosylamino)-2-$R_1$-N-$R_2$-N-$R_3$-acetamide according to claim 1 or a pharmaceutically acceptable acid addition salt thereof and a pharmaceutically acceptable vehicle.

* * * * *